(12) United States Patent
Block

(10) Patent No.: US 8,235,956 B2
(45) Date of Patent: Aug. 7, 2012

(54) PACKAGING AND KIT FOR A FEMALE URINE VOIDING APPARATUS

(75) Inventor: James C. Block, Maple Plain, MN (US)

(73) Assignee: FemMed, Inc., Minnetonka, MN (US)

( * ) Notice: Subject to any disclaimer, the term of this patent is extended or adjusted under 35 U.S.C. 154(b) by 440 days.

(21) Appl. No.: 12/495,399

(22) Filed: Jun. 30, 2009

(65) Prior Publication Data

US 2010/0331798 A1    Dec. 30, 2010

(51) Int. Cl.
*A61F 5/44* (2006.01)

(52) U.S. Cl. ........ 604/329; 604/331; 206/406; 206/407; 206/413; 206/414; 206/423; 206/446; 206/524.1; 206/822; 53/451

(58) Field of Classification Search .................. 604/329, 604/389, 331; 206/407, 406, 413, 414, 423, 206/446, 822, 524.1; 53/451
See application file for complete search history.

(56) References Cited

U.S. PATENT DOCUMENTS

| | | | | |
|---|---|---|---|---|
| 2,975,888 A | * | 3/1961 | Paynton, Sr. | .................. 206/771 |
| 3,225,805 A | * | 12/1965 | Wise | ............................. 150/118 |
| 3,913,774 A | * | 10/1975 | Vajtay | .......................... 220/4.01 |
| 4,014,723 A | * | 3/1977 | Jones | ............................... 156/69 |
| 4,051,992 A | * | 10/1977 | Bergstein | .................. 229/162.5 |
| 4,484,917 A | | 11/1984 | Blackmon | |
| 4,524,565 A | * | 6/1985 | Palm | ............................... 53/449 |
| 4,568,339 A | | 2/1986 | Steer | |
| 4,795,449 A | | 1/1989 | Schneider et al. | |
| 4,802,577 A | * | 2/1989 | O'Leary | ........................ 206/278 |
| 4,822,347 A | | 4/1989 | MacDougall | |
| 5,632,736 A | | 5/1997 | Block | |
| 5,641,064 A | * | 6/1997 | Goserud | .................... 206/315.1 |
| 5,655,658 A | * | 8/1997 | Saveliev et al. | ............... 206/407 |
| 5,791,473 A | * | 8/1998 | Decker et al. | .................. 206/407 |
| 5,813,529 A | * | 9/1998 | Goserud | .................... 206/315.1 |
| 5,819,936 A | * | 10/1998 | Saveliev et al. | ............... 206/407 |
| 6,631,801 B2 | * | 10/2003 | Boyd-Moss et al. | .......... 206/204 |
| 6,928,793 B2 | * | 8/2005 | Rutledge | ......................... 53/449 |
| 2003/0233079 A1 | | 12/2003 | Parks et al. | |
| 2004/0004053 A1 | * | 1/2004 | Zurcher | ......................... 215/364 |
| 2005/0010182 A1 | | 1/2005 | Parks et al. | |
| 2006/0207905 A1 | * | 9/2006 | Whiteside | ..................... 206/434 |

\* cited by examiner

*Primary Examiner* — Tatyana Zalukaeva
*Assistant Examiner* — Ginger T Chapman
(74) *Attorney, Agent, or Firm* — Hamre, Schumann, Mueller & Larson, P.C.

(57) ABSTRACT

Packaging for an extra-labial fluid voiding apparatus includes a tube having a cylindrical wall, a closed end, and an open end. The cylindrical wall and closed end define a cavity that can contain the voiding apparatus. The cylindrical wall is pliable and has an inner diameter. A cap is adapted to respectively close and open the tube at the open end. The cap has an end plate with an annular flange extending therefrom. The annular flange is rigid and has an outer diameter. The annular flange is insertable into the cavity at the open end of the tube and within the inner diameter of the cylindrical wall. The outer diameter of the flange is larger than the inner diameter of the cylindrical wall to a degree such that the outer diameter and the inner diameter are engageable in a press-fit arrangement, when the cap is connected to the tube.

18 Claims, 10 Drawing Sheets

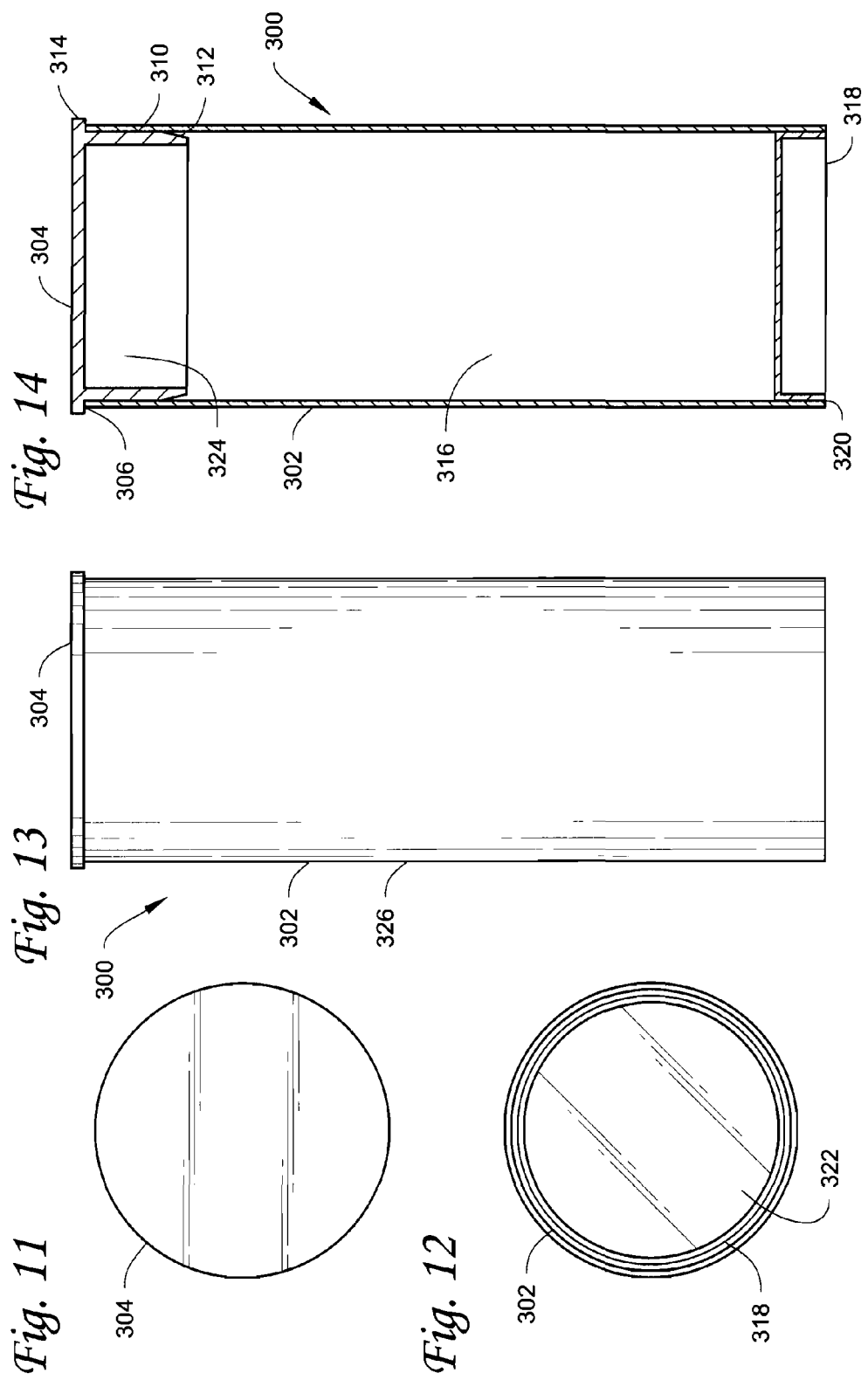

PACKAGING AND KIT FOR A FEMALE URINE VOIDING APPARATUS

RELATED APPLICATIONS

This application is related to Ser. No. 10/839,723, which is a Continuation-in-Part of Ser. No. 10/453,316, filed Jun. 3, 2003, which claims the benefit of priority of Provisional Application Ser. No. 60/390,685, filed Jun. 18, 2002, all of which are incorporated by reference in their entirety.

FIELD

The disclosure herein relates generally to fluid voiding apparatuses. More particularly, the disclosure relates to a unique packaging and kit for an extra-labia fluid voiding apparatuses.

BACKGROUND

The prior art discloses a variety of sanitary devices that are designed to allow females to void urine while standing up in order to avoid non-hygienic contact with toilet facilities. Such devices often include substantially rigid funnel structures adapted to cover the vulval region of a female anatomy. However, such substantially rigid funnel structures are typically bulky, not readily disposable, and require a user to hold the funnel structure against the body during urination in order to maintain a fluid tight seal thereby increasing the possibility of misdirecting the urine from the end of the funnel. Further, a user of such devices can experience uncomfortable side effects from urine splashing back at the user off the sidewall of the funnel structure, which may also lead to leakage out of the device, particularly where the seal is intended between the user and the device.

U.S. Pat. No. 4,568,339 discloses a female incontinence device including a generally funnel shaped receiving member that defines a groove into which an adhesive paste is disposed to provide a seal to prevent urine leakage. The device can be reused by replacing the adhesive paste each time the device is used.

U.S. Pat. Nos. 4,484,917; 4,795,449; and 4,822,347 each disclose female incontinence devices having inter-labia adhesive sealing structures. Such incontinence devices are typically designed as catheters for long term use.

U.S. Pat. No. 5,632,736 to Block discloses an extra-labia urine voiding apparatus including a container sized and shaped to externally cover a vulval region of a female anatomy. The container defines a reservoir and includes an open side that is adapted for receiving urine into the reservoir. The container also includes a flange having a substantially planar surface adapted to face and generally surround a periphery of the vulval region. An extra-labia sealing structure is affixed to the planar surface of the flange. The sealing structure includes a pressure sensitive adhesive adapted to provide a generally fluid tight primary adhesive seal between the container and external tissue generally surrounding the vulval region. The voiding apparatus also includes a conduit adapted for draining urine from the reservoir.

Although these devices may be suitable for their intended uses, improvements may still be made in providing a fluid voiding apparatus that prevents uncomfortable splash back at a user, while maintaining a fluid tight seal between the device and the user to prevent leakage. A fluid voiding apparatus is desired that provides optimum convenience for use and transport, and is cost effective for manufacture.

Improvements may also be made to kits employing a fluid voiding apparatus, including improvements to the overall packaging structure, user friendliness, and attractiveness of such kits.

SUMMARY

Generally, various improvements upon existing female urine voiding devices are described herein including, for example, a female fluid urine voiding apparatus having a blocking mechanism capable of preventing urine voided from a user's body from splashing back at the user. Additionally, improvements to kits that include the urine voiding apparatuses described herein are disclosed. Such improvements include, for example, the overall packaging structure, user friendliness, and attractiveness of such kits.

In one embodiment, packaging for an extra-labial fluid voiding apparatus includes a tube having a cylindrical wall, a closed end, and an open end. The cylindrical wall and closed end define a cavity that can contain the voiding apparatus. The cylindrical wall has an inner diameter. A cap is adapted to respectively close and open the tube at the open end. The cap has an end plate with an annular flange extending therefrom. The annular flange has an outer diameter. The annular flange is insertable into the cavity at the open end of the tube and within the inner diameter of the cylindrical wall. The outer diameter of the flange is larger than the inner diameter of the cylindrical wall to a degree such that the outer diameter and the inner diameter are engageable in a press-fit arrangement, when the cap is connected to the tube.

In one embodiment, the packaging structure is used for a kit to contain an extra-labial urine voiding. In some embodiments, the kit will contain a piece of absorbent material and a bag configured for containing the extra-labial urine voiding apparatus and piece of absorbent material after usage.

In one embodiment, the cylindrical wall is pliable and the annular flange is rigid. In other embodiments, the cap is an entirely rigid structure and the tube overall is less rigid than the cap.

In some embodiments, the annular flange includes a leading end configured to enter the tube first when the cap is connected to the tube, where the leading end has a ramp surface extending annularly inward from the outer diameter.

It is to be understood that both the foregoing general description and the following detailed description are exemplary and explanatory only, the details of which are not intended to be restrictive.

BRIEF DESCRIPTION OF THE DRAWINGS

Referring now to the drawings in which like reference numbers represent corresponding parts throughout:

FIG. 11 is an end view of the packaging structure of FIG. 9 taken from the cap end.

FIG. 12 is an end view of the packaging structure of FIG. 9 taken from the end opposite the cap end.

FIG. 13 is a side view of the packaging structure of FIG. 9. showing the cap connected to the tube.

FIG. 14 is a sectional view of the packaging structure of FIG. 9 showing the press fit of the cap and the tube.

DETAILED DESCRIPTION

Figure 1:
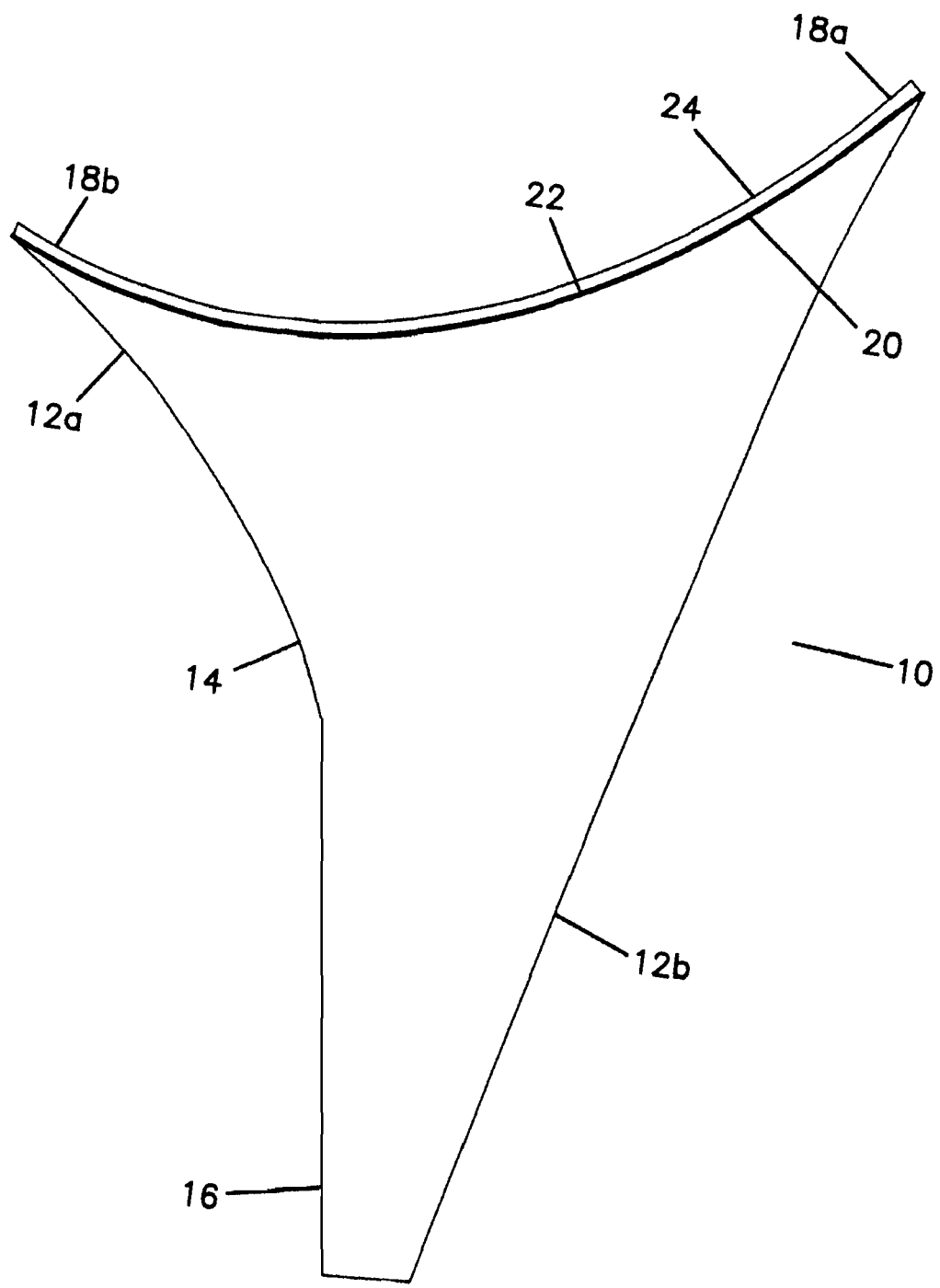
FIG. 1 represents an elevational side plan view of one embodiment of a urine voiding apparatus.

FIGS. 1-4 show one embodiment of a urine voiding apparatus 10 constructed in accordance with the inventive concepts herein. The urine voiding apparatus 10 includes a container 14 having top 12a and bottom 12b portions. The top 12a is sized and shaped to cover a vulval region of a female anatomy. The container 14 defines a reservoir 50 between the top 12a and bottom 12b adapted for receiving urine, where the reservoir 50 is in fluid communication with an open side 13 disposed at the top 12a of the container 14. The open side 13 allows urine discharged from a user's urethral orifice to be received into the reservoir 50.

Preferably, the urine voiding apparatus 10 includes a conduit 16 adapted for draining urine from the container 14 and reservoir 50. More preferably, the conduit 16 is integrally formed with the container 14 and is disposed proximate the bottom 12b of the container 14. An opening 52 resides at the bottom 12b of the container 14 enabling urine to be drained through the conduit 16 and out of the urine voiding apparatus 10.

A planar surface 20 is connected to the top 12a of the container 14 and extends generally about a perimeter of the open side 13 defined by the container 14. In one embodiment, an extra-labia sealing structure such as a pressure sensitive adhesive 22 is connected to the container 14 and is disposed on the planar surface 20. The extra-labia sealing structure extends generally around the perimeter of the open side 13. The pressure sensitive adhesive 22 is adapted for forming a generally fluid tight seal around a periphery of a user's vulval region, and prevents urine from leaking between the container 14 and a user's body. Optionally, a raised ridge 28, substantially resembling a rib-like structure or protrusion, is may be disposed proximate the top 12a of the container 14 on the planar surface 20 and about the perimeter of the outer surface of the container 14. The raised ridge 28 is adjacent the pressure sensitive adhesive 22. The raised ridge 28 assists in preventing leakage from the urine voiding apparatus 10 when the apparatus is supported against the periphery of a user's vulval region during use. It will be appreciated that a raised ridge resembling raised ridge 28 could also be included on the planar surface 20 at an inner perimeter of the planar surface 20. The pressure sensitive adhesive 22 also provides a structure such that use of the urine voiding apparatus may be hands free. It will be appreciated a pressure sensitive adhesive may not be employed, and a user may simply fit and press the planar surface 20 to the periphery of the vulval region as necessary to manually hold the urine voiding device 10 in place to provide a suitable seal.

Figure 2:
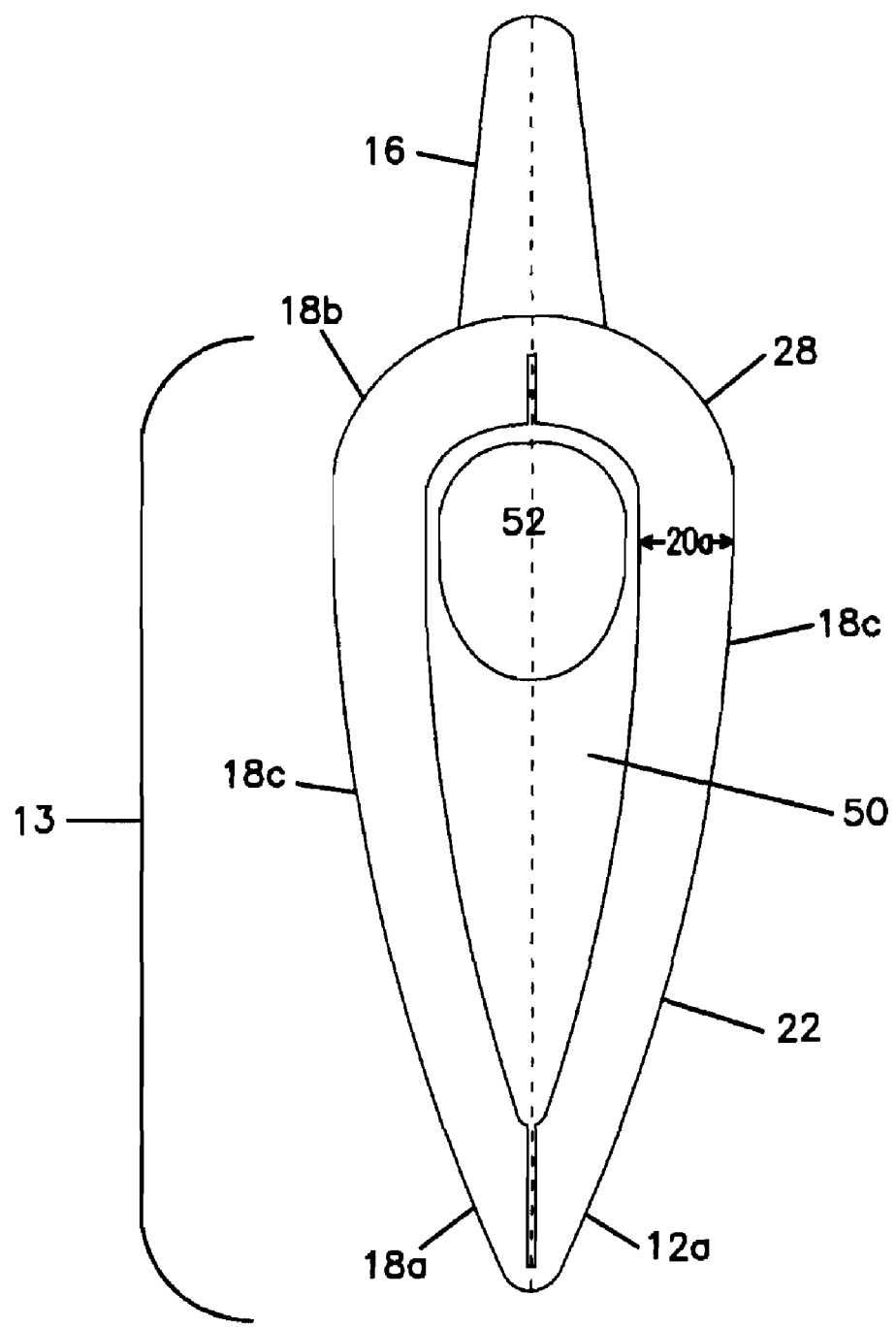
FIG. 2 represents an elevational top plan view of the urine voiding apparatus of FIG. 1.

As above, the container 14 includes the top 12a being sized and shaped to cover a vulval region of a female anatomy. As best shown in FIG. 2, the container 14 of the urine voiding apparatus 10 has a generally oval planform that defines the open side 13 and the reservoir 50 adapted for receiving urine. It will be appreciated that the planform of the container 14 also may be other shapes adaptable for covering the vulval region of a female anatomy. For example such shapes include, but are not limited to a triangular shape or hourglass shape.

Preferably, the top 12a is arranged and constructed in a curved configuration as best shown in FIG. 1, such that the top 12a is concave toward the reservoir 50. It will be appreciated that the degree of curvature of the top 12a may vary as needed. The container 14 includes a superior end 18b adapted to align generally with the mons Veneris of the female anatomy and an inferior end 18a adapted to align generally with the perineal region of the female anatomy. Extending between the superior end 18b and the inferior end 18a of the container 14 are opposing outwardly curved sides 18c that are arranged and configured to generally align along the labium majus of the female anatomy.

It will be appreciated the planar surface 20 and the extra-labia sealing surface 22 substantially conform to the planform of the urine voiding apparatus 10.

Figure 3:
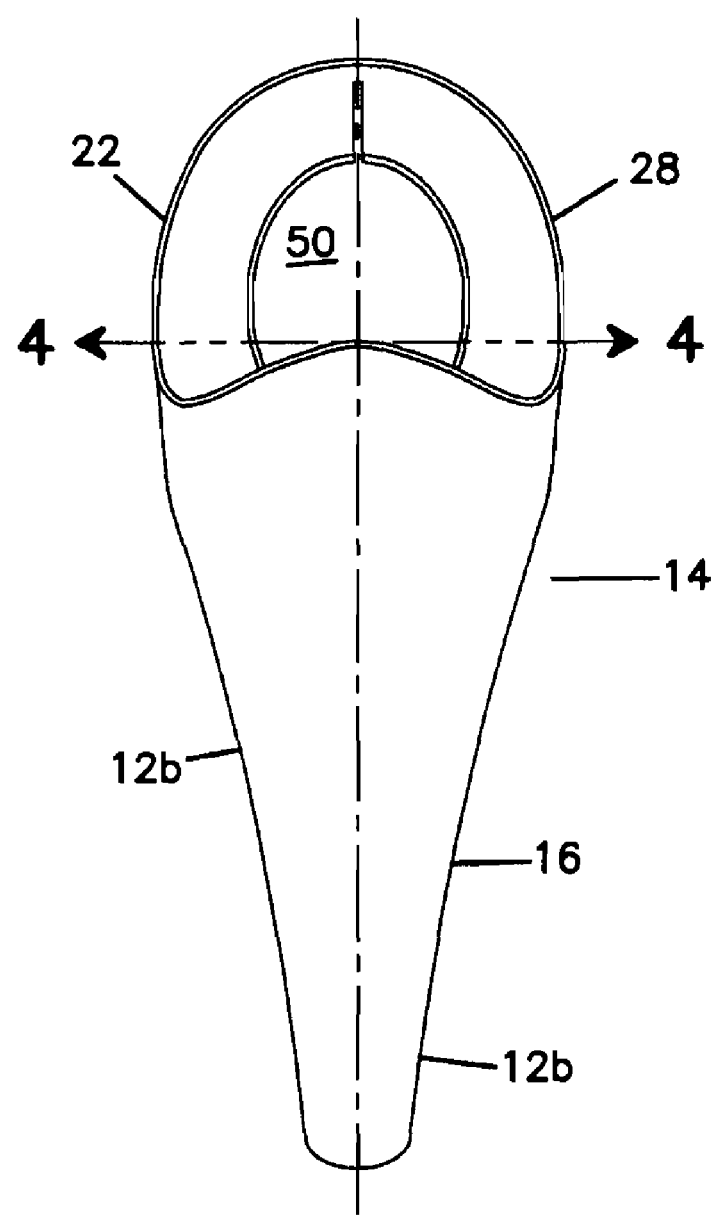
FIG. 3 represents an elevational top perspective view of the urine voiding apparatus of FIG. 1.
Figure 4:
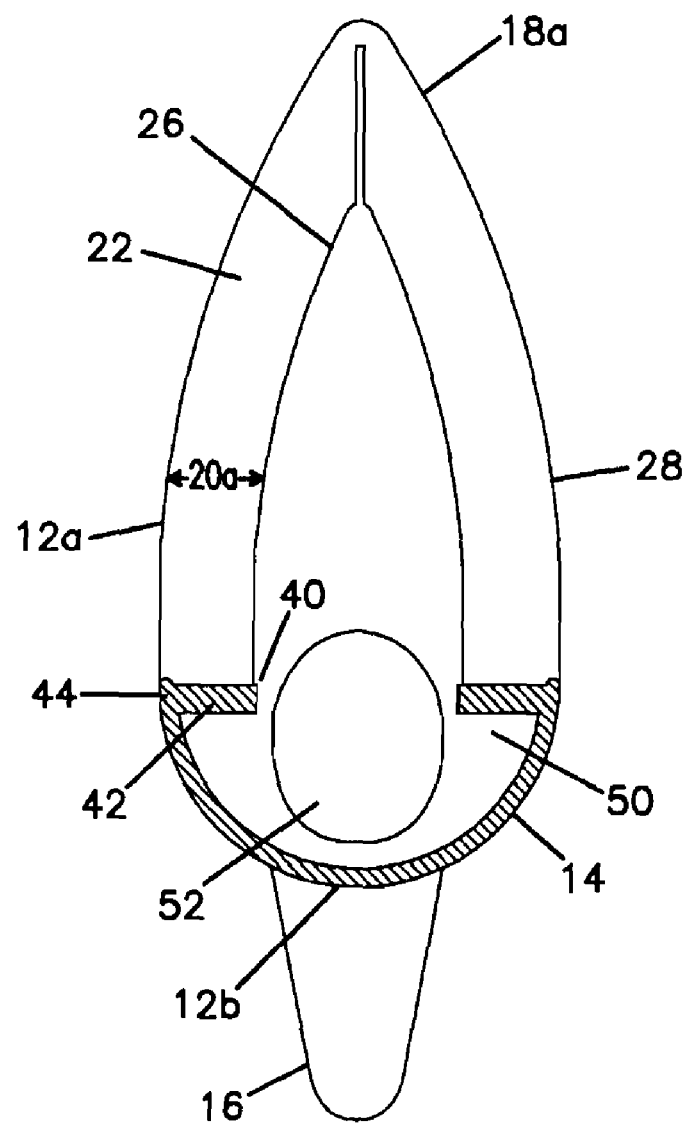
FIG. 4 represents a partial sectional view of the urine voiding apparatus of FIG. 1.

Preferably, the planar surface 20 of the container 14 surrounds the perimeter of the open side 13 at the top 12a of the container 22 and is adapted to face and generally surround a user's vulval region. Optionally, the planar surface 20 resides on a flange or rim 26. As above in FIGS. 1-4, a raised ridge 28, substantially resembling a rib-like structure or protrusion, is preferably disposed proximate the top 12a of the container 14 on the planar surface 20 and about the perimeter of the outer surface of the container 14. The raised ridge 28 is adjacent the pressure sensitive adhesive 22. The raised ridge 28 assists in preventing leakage from the urine voiding apparatus 10 when the apparatus is supported against the periphery of a user's vulval region during use. Preferably, as best shown in FIGS. 3 and 4, the planar surface 20 extends inwardly from the outer surface and perimeter of the container 14. It will be appreciated the planar surface 20 also may be a flange or rim extending outwardly (not shown) from the outer surface and perimeter of the container 14, so as to overhang past the outer surface and perimeter of the container 14. The planar surface 20 includes a width 20a, where the width 20a provides suitable contact area for the optional pressure sensitive adhesive 22 to be affixed to the planar surface 20 and thereby suitably contact a user's vulval region when the urine voiding apparatus 10 is in use. The urine voiding apparatus may also be used without any adhesive.

In one embodiment, the pressure sensitive adhesive 22 of the urine voiding apparatus 10 is a gel-like material affixed to the planar surface 20 of the container 14. Preferably, the pressure sensitive adhesive 22 is directly applied to the planar surface 20 of the container 14. More preferably, the pressure sensitive adhesive is covered with a non-stick backing 24, such as the backing conventionally used on stickers. The backing 24 prevents the pressure sensitive adhesive 22 from adhering to objects when the urine voiding apparatus 10 is not being used. Examples of suitable materials employed for construction of the pressure sensitive adhesive 22 may include but are not limited to 3M Hydrogel and 3M Hydrocolloid 9943. More preferably, the adhesive 22 is a hydrocolloid adhesive, such as Hydrocolloid Adhesive by Avery Dennison MED 2191H. FIGS. 2-4 illustrate the apparatus without the backing 24. It will be appreciated that these materials are merely exemplary as other adhesive materials also may be suitable.

It will be appreciated that other materials may be employed in providing the pressure sensitive adhesive 22. For example, a double-sided adhesive tape (not shown) may be employed that includes a carrier film having opposing sides coated with adhesive. A first side of such an adhesive tape would be affixed to the planar surface 20 of the container 14 such that the adhesive extends completely around the perimeter of the open side 13 of the container 14. A second side of the adhesive tape would be adapted to provide a generally fluid tight primary adhesive seal between the container 14 and a user's external tissue generally surrounding the vulval region.

It is preferred that the pressure sensitive adhesive 22 has a greater bond strength with respect to the container 14 or with respect to a carrier film the pressure sensitive adhesive 22 may reside on than a bond strength with respect to the external tissue surrounding the vulval region. Such a difference in bond strength causes substantially no adhesive residue to remain on the external tissue surrounding the vulval region after the urine voiding apparatus 10 is used. Preferably, the pressure sensitive adhesive 22 is permanently affixed to the planar surface 20 of the container 14 such that the adhesive 22 will not pull away from the container 14 when the voiding apparatus 10 is removed from the vulval region.

When the urine voiding apparatus 10 is placed over the vulval region of the female anatomy, the pressure sensitive adhesive 22 forms a generally fluid tight seal between the container 14 and external tissue generally surrounding the vulval region of a user such as the tissue of the mons Veneris, labium majus and the tissue of the perineum. In operation, while the pressure sensitive adhesive 22 contacts the vulval region so as to press against the vulval region, the pressure sensitive adhesive 22 holds the container 14 to the external tissue the planar surface 20 surrounds to prevent leakage between the urine voiding apparatus 10 and the external tissue of the vulval region. Further, the pressure sensitive adhesive 22 can allow for the urine voiding apparatus to be a hands-free unit when in use. As above, it also will be appreciated an adhesive may not be employed, and a user may simply fit and press the planar surface to the periphery of the vulval region as necessary to manually hold the urine voiding device 10 in place to provide a suitable seal.

As shown in FIG. 4, the optional blocking mechanism 40 includes a wall 44 connected to the container 14 and facing the reservoir 50. The wall 44 is generally disposed proximate the open side 13 of the container 14 about a perimeter of the reservoir 50 and extends a distance inward from the perimeter of the reservoir 50. The wall 44 includes a blocking surface 42 thereon, in which the blocking surface 42 provides a front that counters urine voided from a user's body from escaping through the open side 13 of the container 14 and contacting the user. Particularly, the blocking surface 42 prevents splash back of urine already voided from a user's body that may bounce off or reflect off the sidewalls and boundaries of the inside of the container, thereby at least reducing and substantially eliminating any uncomfortable effects from such conditions.

The wall 44 defines an overlap covering a portion of the reservoir 50 proximate the open side 13. The overlap is arranged and constructed such that the open side 13 and reservoir are not obstructed from receiving urine discharged from a user's body. More preferably, the wall 44 and blocking surface 42 substantially are flat shaped and perpendicular to the direction of flow through the opening 52 and conduit 16.

As shown in FIG. 4, the blocking mechanism 40 may be directly opposite from the planar surface 20, and the blocking mechanism 40 is substantially parallel with the open side 13 and planar surface 20 of the container 14. Preferably, the wall 44 extends to the opening defined by the open side 13. It will be appreciated that the configuration illustrated in FIG. 4 is merely exemplary as other configurations also may be employed.

In operation, the blocking mechanism 40 prevents urine voided from a user's body from escaping through the open side 13 of the container 14 and contacting the user. Additionally, the blocking mechanism 40 can assist the raised ridge 28 in preventing leakage, as urine is blocked from exiting out of the open side 13 at the top 12a of the container 14.

It will be appreciated that the container 14 is preferably compact to facilitate carrying the urine voiding device, for instance, in a purse, daypack, travelbag or the like. It will be appreciated that the container 14 may be constructed of a rigid, semi rigid, or flexible material to further facilitate carrying the urine voiding apparatus 10. Preferably, the material used to produce the container 14 is a light weight material. The container 14 may be manufactured of a plastic, rubber or latex material. More preferably, the container 14 is constructed of a flexible and foldable material so that the urine voiding apparatus 10 may be packaged in a compact size for convenience in handling and transport. Preferably, the urine voiding apparatus may be folded to a dimension of 1.75×3.5× 1.25 inches. The container may be formed from Dow Corning Q7-4750 LSR (Liquid Silicone) or General Electric LIM® (Liquid Injection Molding) 6071. Preferably, the container is formed from 60 durometer silicone. Alternatively, the material used for producing the container may be a thermoplastic elastomer compound such as Dynaflex G6713-0001 by GLS Corp. It will be appreciated that the above materials are exemplary only, as other materials may also be suitable for the manufacture of the container 14. Preferably, the material used for producing the container has material properties that allow the apparatus to spring back to its original form after storage in a folded configuration. This feature may be achieved with a silicone rubber.

It will be appreciated that the volume of the reservoir 50 and the diameter of the conduit 16 can be varied to achieve a desired voiding pressure within the container 14. Further, the length of the conduit 16 may vary, and the conduit 16 may be adapted for attachment to a line (not shown). Additionally, various embodiments of the fluid voiding apparatus 10 can be constructed having pressure sensitive adhesives 22 of different adhesive bond strengths. The adhesive bond strengths will vary depending upon a variety of factors such as skin sensitivity, voiding pressures, the dimensions of the voiding apparatus 10, and the particular application. For example, a stronger adhesive bond strength may be required to provide a total hands-free seal as compared to an adhesive that is used to provide a manually assisted seal.

It will also be appreciated that the urine voiding apparatus 10 can be constructed in various sizes so that the proper apparatus can be chosen for a best fit. It will further be appreciated that the urine voiding apparatuses 10 of different sizes and shapes can be manufactured in different colors corresponding to a particular size so as to color code the urinary voiding apparatuses 10. If an adhesive is used, color coding can also be used to indicate different adhesive bond strengths.

Figure 5:
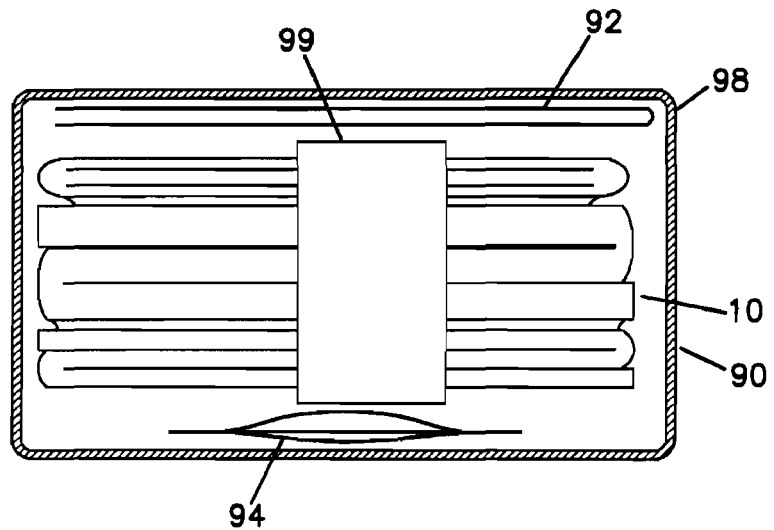
FIG. 5 represents a schematic sectional view of one embodiment of a urine voiding apparatus incorporated in a kit.
Figure 8:
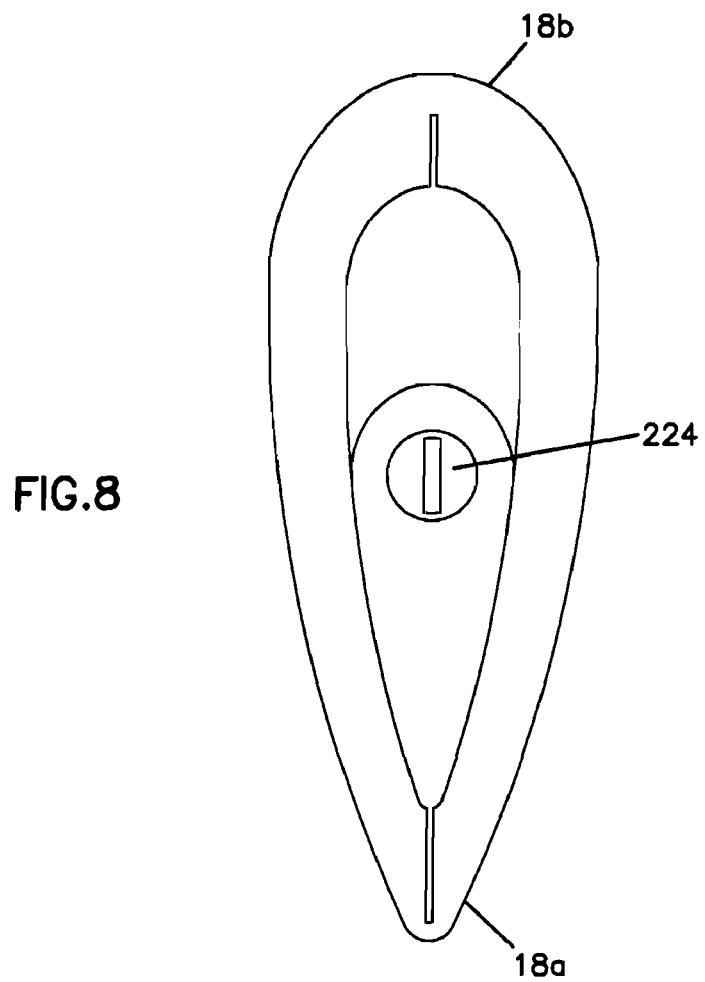
FIG. 8 represents a top view of a urine voiding apparatus.

FIG. 5 shows one example of a urine voiding kit 90 incorporating a urine voiding apparatus 10 in accordance with the inventive concepts herein. The features of the urine voiding device 10 include the same features as described above for the urine device 10, and are not further discussed. The kit 90 also includes a packaging container 98. The packaging container 98 may be constructed using well known structures and methods. For example, the packaging container may be "pegable" chipboard box, i.e. a box that can be presented in a store hanging on a peg. The box may also be formed from cardboard or paper cardstock. Preferably, a piece of material 94 adapted for wiping the vulval region after urination is included and packaged along with the urine voiding device 10 in the container 98. The material is preferably a moist antibacterial towelette but could also be a napkin or tissue wipe. For example, a moistened antibacterial towelette containing 0.2% Benzethonium Chloride as the active ingredient may be used. In active ingredients may include Aloe Vera Extract, Apricot Extract, Bezalkonium Chloride, water, and other ingredients. Alternatively, absorbent material may be used. It will be appreciated that the kit 90 may not be resealable and the urine voiding device 10 and kit 90 may both be readily discarded after use. It will also be appreciated that the structure and configuration of the kit 90 may be varied.

In practice, the kit 90 is preferably sized so as to be easily carried, for instance in a purse or the like. As above, the urine voiding apparatus may be folded in a compact size for convenience in handling and transport. Preferably, the urine voiding apparatus is folded to a dimension of 1.75×3.5×1.25 inches and can be restrained by a band 99. In use, a female removes the urine voiding apparatus 10 from the sealed packaging container 98. The urine voiding apparatus 10 is then placed over the vulval region and the planar surface 20 is pressed toward the body to form a generally fluid tight seal between the planar surface 20 and the external tissue generally surrounding the vulval region. Urine is received in the reservoir 50 of the container 14, and is directed away from the user's body through the opening 52 and the conduit 16.

The user may simply fit and press the planar surface to the periphery of the vulval region as necessary to manually hold the urine voiding device 10 in place and provide a suitable seal. A user can focus attention on directing the urine traveling through the conduit 16 to a particular location, such as a toilet.

After the voiding process is complete, the user removes the urine voiding apparatus 10 from the vulval region and dries the vulval region with the wipe 94. Finally, the wipe 94 and the urine voiding apparatus 10 are placed in a separate bag 92. The separate bag 92 is employed and adapted for containing the urine voiding apparatus 10 and piece of material 94 after usage. The bag may be sealable for example by a zip-lock mechanism, by tying the bag in a knot, or by other methods known to those skilled in the art. The bag may also be sealed with a twist tie, i.e. a short length of wire encased in a strip of paper, plastic, or foil, designed to be twisted around an item or items as a fastener. It will be appreciated that the urine voiding apparatus 10 and the packaging container 98 also may be discarded immediately after use.

As above, the inventive concepts herein provide an efficient urine voiding apparatus for use by females which is light weight and compact so that it can be conveniently carried while occupying a minimum amount of space, such as in a purse. Further, a urine voiding apparatus is provided with a blocking mechanism that prevents uncomfortable splash back of urine at the user when the apparatus is being used during urination. The inventive concepts herein also provide a urine voiding apparatus that is usable while disturbing a minimum amount of garb by the user, and is sanitary and readily disposable after use.

Figure 6:
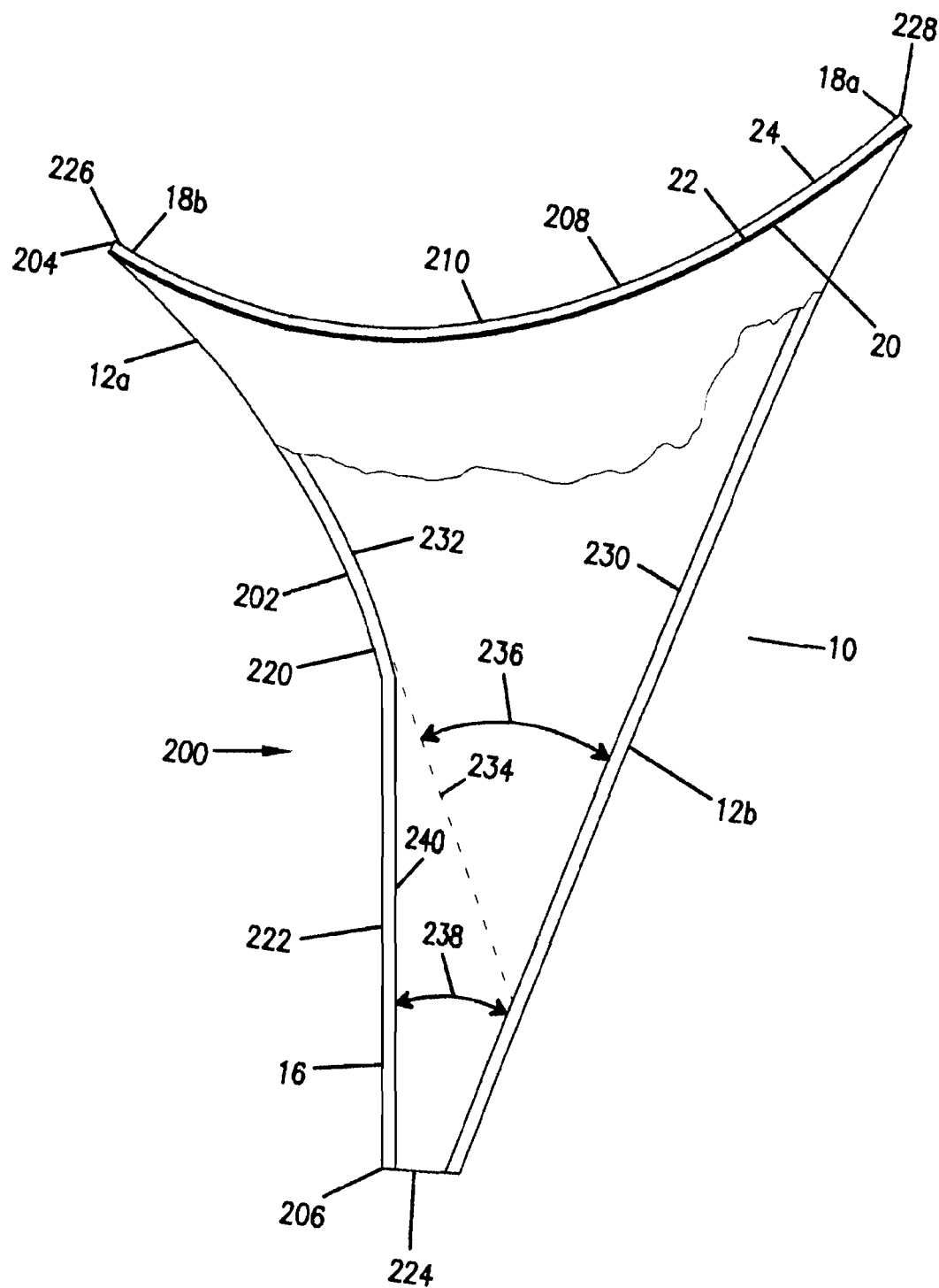
FIG. 6 represents a partially cutaway elevational side plan view of a preferred embodiment of a urine voiding apparatus.
Figure 7:
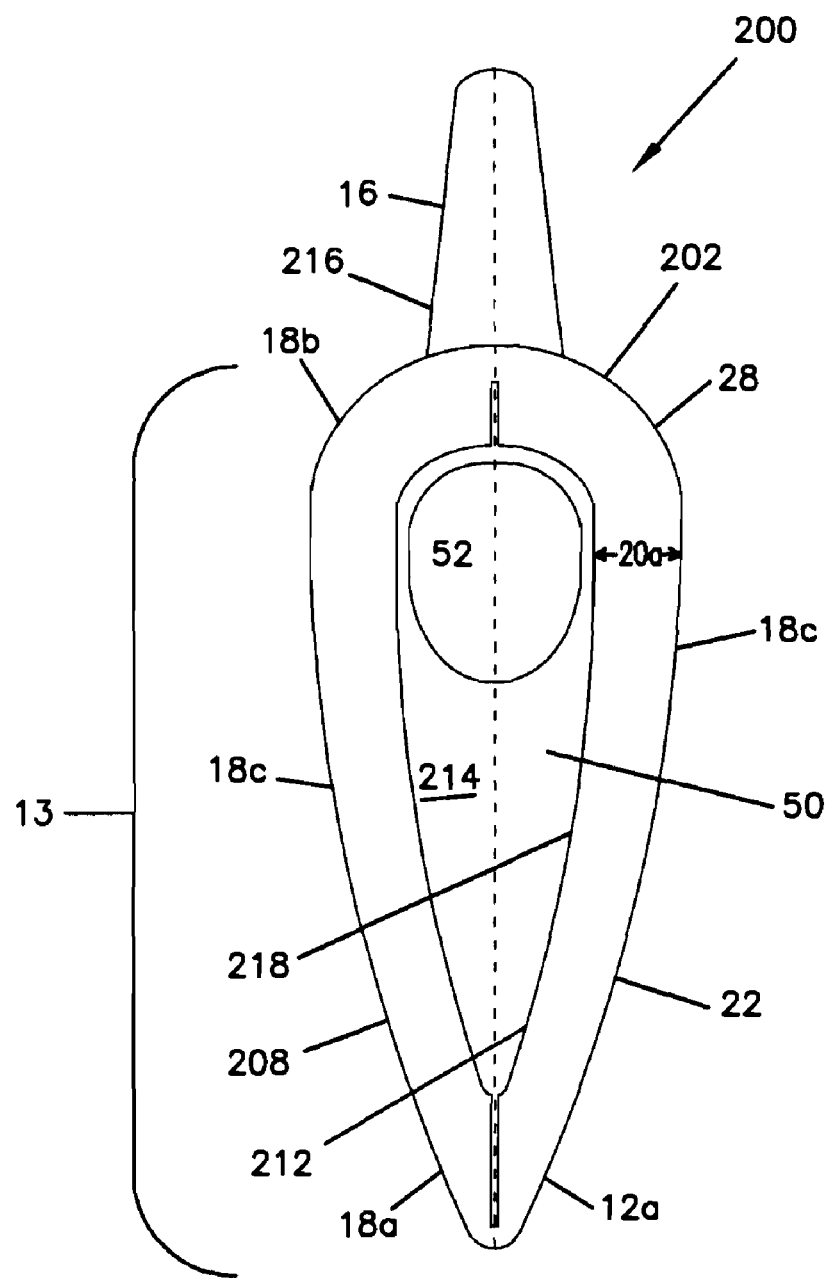
FIG. 7 represents an elevational top plan view of the urine voiding apparatus of FIG. 6.

FIGS. 6 and 7 show a preferred extra-labia urine voiding apparatus 200. The apparatus includes a container 202 having a top 204 and a bottom 206. The top is sized and shaped to cover a vulval region of a female anatomy. An upper surface 208 at the top 204 of the container 202 is arranged to face and generally surround a periphery of the vulval region. The top includes an open side 210 which has an opening 212 for receiving urine into the apparatus 200. The opening 212 is shown in FIG. 7.

The container has interior surfaces 214 and exterior surfaces 216. The interior surfaces define a reservoir 218 on the interior of the apparatus 202. The reservoir is tapered from the opening 212 to a narrower portion 220 lower in the container 202. Below the reservoir, a conduit 222 extends generally downwardly to the bottom of the container. At the end of the conduit is an opening 224 for draining urine from the container 202. Optionally, a pressure sensitive adhesive may be affixed to the upper surface 208 for promoting an adhesive seal between the container and local tissue.

Preferably, the container 202 and conduit 222 are formed from an opaque material so that a user cannot see the flow of urine through the container and conduit. The container and conduit are also preferably formed from a resilient substance, so that the apparatus may be rearranged, i.e., folded, into a compressed configuration for storage without substantial permanent deformation of the apparatus. Depending on the material selected, the apparatus may spring back to its original configuration when restraints such as a box or paper band 99 are removed. Silicone rubber, for example, provides good shape memory to allow the apparatus to return to its original shape when removed from a storage container. In one embodiment the apparatus is folded into a compressed configuration and maintained in that configuration with the restraint such as a piece of paper looped around the apparatus and adhered to itself with an appropriate adhesive.

The apparatus has a front side 226 and a back side 228. The opening 212 is wider at the front side than at the back side.

The interior surface defines a generally linear path 230 that extends from the opening on the top of the container to the opening 224 in the bottom of the container. Preferably the apparatus is symmetric about a plane that passes through the path 230. The interior surfaces of the apparatus also define a front surface 232 at the front side of the apparatus. The front surface 232 defines a front surface axis 234. In the preferred embodiment, the front surface axis 234 and the path 230 form an angle of approximately 50 degrees. Preferably, as shown in FIG. 6, the path 230 extends through both a reservoir and a conduit to promote fluid flow out of the apparatus.

The conduit preferably includes a surface 240 opposed to the path that defines an axis which is offset from the path by an angle 238 of approximately 22 degrees. The generally linear path 230 is preferably between 5½ and 7½ inches long. The front surface 232 near the opening preferably extends for 2 to 3 inches. The conduit surface 240 also preferably extends for 2 to 3 inches. The above-described surfaces are generally smoothly contoured. The surfaces are not necessarily linear but the overall configuration and orientation of the surfaces operates to promote efficient flow of urine through the apparatus with minimal splash back.

The apparatus is available in a kit as previously described. The bag preferably includes a mechanism for sealing a used apparatus in the bag, such as a zip-lock sealing mechanism, a twist tie or handles for tying the bag. The apparatus may be provided in packaging which combines a plurality of kits. For example the kits may be provided in a box which contains 35 or up to 100 kits or more. The material provided in the kits is preferably material impregnated with anti-bacterial substance. For example an anti-bacterial towelette may be provided in a sealed package within the kit.

Packaging and Kit Improvements

FIGS. 9-15 show another embodiment of a packaging structure 300 for a kit that contains the female urine voiding apparatus as already illustrated and described (e.g. 200 shown in FIGS. 6 and 7). Generally, the packaging structure includes a cap and tube that are engageable in a press fit connection when the packaging is to be closed, and the cap and tube are releasable from one another when the packaging needs to be opened. The packaging structure described herein can enjoy such benefits as, for example, convenient transport, user friendliness, and overall attractiveness of the kit.

Figure 10:
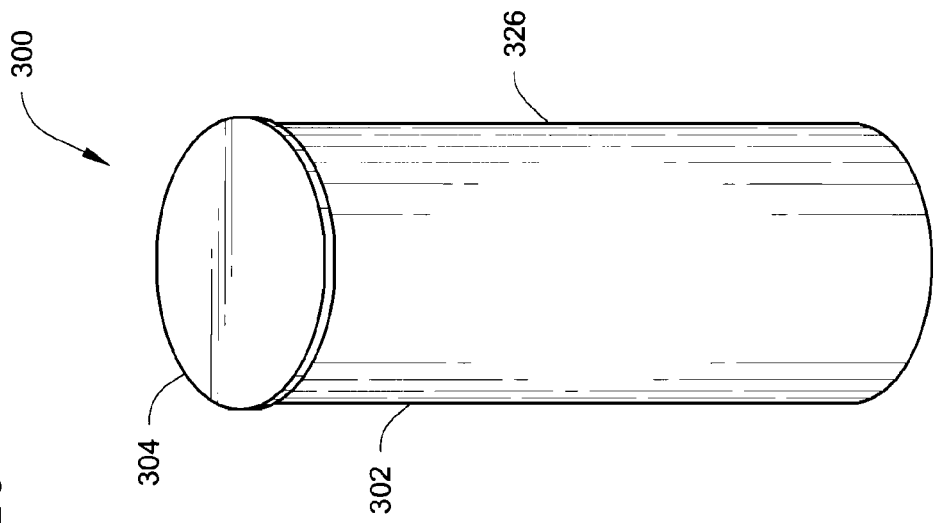
FIG. 10 is a top perspective view of the packaging structure of FIG. 9 showing the cap connected to the tube.
Figure 9:
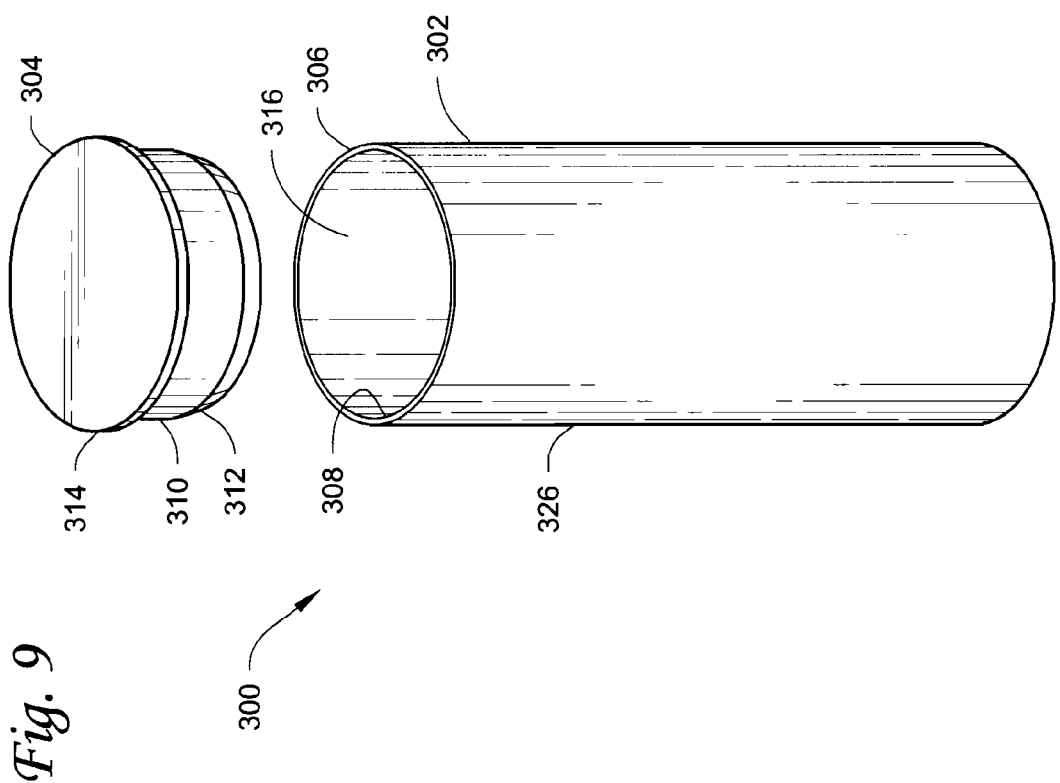
FIG. 9 is an exploded perspective view of one embodiment a packaging structure for a urine voiding apparatus, showing a tube and a cap.

In the embodiment shown, the packaging 300 for an extra-labial fluid voiding apparatus includes a tube 302 constructed as a cylindrical wall 326, a closed end 318, and an open end opposite the closed end. The cylindrical wall 326 and closed end 318 define a cavity 316 that can contain a voiding apparatus. The cylindrical wall 326 has an inner surface defining an inner diameter 308. A cap 304 is adapted to respectively close and open the tube 302 at the open end. FIG. 9 shows the tube 302 and cap 304 in an exploded perspective view, and FIGS. 10, 13, and 14 show the cap 304 connected to the tube 302.

The cap 304 has an end plate with an annular flange 310 extending therefrom (see e.g. end view of the cap in FIG. 11 and sectional view of FIG. 14). The annular flange 310 has an outer surface defining an outer diameter. The annular flange 310 is insertable into the cavity 316 at the open end of the tube 302 and within the inner diameter 308 of the cylindrical wall 326.

In a preferred embodiment, the outer diameter of the flange 310 is larger than the inner diameter 308 of the cylindrical wall 326. That is, the outer diameter of the flange 310 is slightly larger than the inner diameter to a degree, such that the outer surface defining the outer diameter and the inner surface defining the inner diameter 308 are engageable in a press-fit arrangement, for example when the cap 304 is to be connected with the tube 302 (see sectional view of FIG. 14). FIG. 14 shows the press-fit engagement of the respective outer and inner surfaces of the annular flange 310 of the cap 304 and the inner cylindrical wall of the tube 302. What is meant by press-fit is that the annular flange 310 and the inner cylindrical wall of the tube 302 are snugly, tightly engaged to suitably connect the cap 304 to the tube 302 until it is removed, for example when manually removed by a user.

Figure 15:
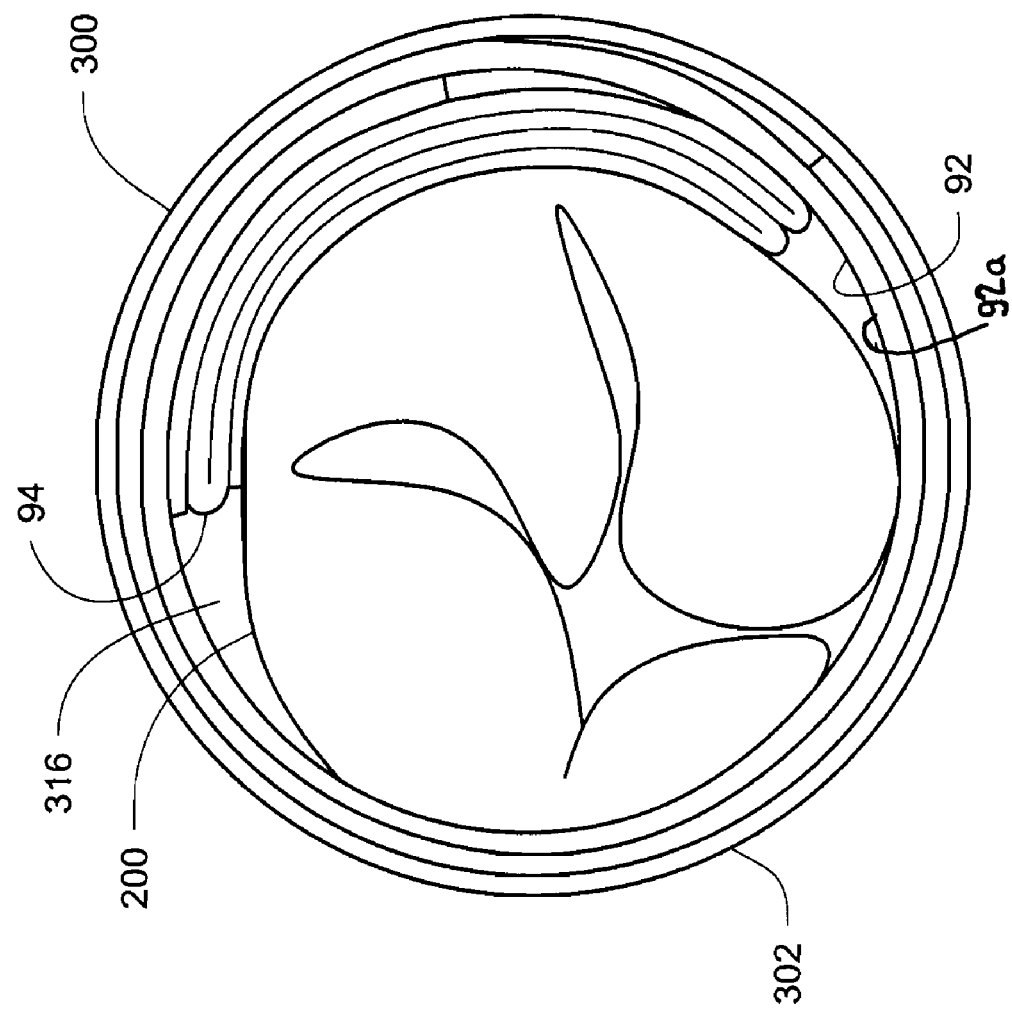
FIG. 15 is an end view of the packaging structure of FIG. 9 taken from the cap end and showing an extra-labial female voiding device contained in the packaging structure, along with an absorbent material, and bag.

As described the packaging structure is configured and arranged to be a part of a kit to contain an extra-labial urine voiding apparatus, for example the apparatus 200. FIG. 15 shows an end view of the packaging structure 300 taken from the end where the cap 304 and shows the extra-labial female voiding apparatus 200 of FIGS. 6 and 7 contained in the packaging structure 300. As shown in FIG. 15, many embodiments will include a piece of absorbent material 94 (e.g. similar to 94 in FIG. 5) as part of the kit.

With further reference to FIG. 15, a bag 92 will be included as part of the kit in many instances. The bag 92 can be similar to the bag 92 of FIG. 5. The bag 92 is configured for containing the extra-labial urine voiding apparatus 200 and piece of absorbent material 94 after usage. In some embodiments, the bag 92 will be constructed of a biodegradable material. In other embodiments, the bag 92 also can include general instructions for use disposed on the bag 92 with information on how to use 92a the kit and its contents. It will be appreciated that the instructions for using the kit can be printed onto the outer surface of the bag 92 in a variety of ways as may be known. The instructions for use can be simple step by step text and/or graphic illustrations to convey how to apply the apparatus, use the apparatus 200 and the piece of absorbent material 94, and then store the apparatus 200 and piece of absorbent material 94 in the bag 92.

With further reference to the overall packaging of the apparatus and its storage, for example after usage, the cavity 316 of the tube 302 is smaller in overall dimension than the extra-labial fluid voiding apparatus 200. As described above, the extra-labial fluid voiding apparatus 200 can be constructed of a shape memory material. With such a construction, the extra-labial urine voiding apparatus 200 can be folded down as needed for containment in the cavity 316 of the tube 302. In some embodiments, the tube 302 and cap 304 together have an overall dimension for a cylinder that is about 3.75 inches in length and about 1.5 inches in diameter. The voiding apparatus 200 can be suitably folded down as needed (e.g. when not in use) so as to fit inside the cavity 316. When needed, the apparatus 200 can be taken out of the packaging 300 and the apparatus will return to its original shape due to its shape memory construction.

With further reference to the press-fit engagement, many suitable arrangements and configurations can help facilitate the press-fit between the cap 304 and the tube 302. For example, the nature of the material and sizing of the tube 302 and cap 304 can be factors to consider when constructing the packaging structure 300. In one preferred embodiment, the cylindrical wall 326 is relatively pliable and the annular flange 310 is relatively rigid. Such a configuration allows the larger outer diameter of the flange 310 to fit into the inner diameter 308 of the cylindrical wall 326 so that the press-fit engagement of their surfaces can occur. In some embodiments, the cap 304 is an entirely rigid structure and the overall tube 302 is less rigid than the cap 302. For example the relative rigidity of the cap 304 can be achieved through construction using various known materials, such as but not limited to plastics. Likewise, the overall lesser rigidity of the tube 302 can be achieved through construction using various materials, such as plastics that are less rigid (e.g. more flexible) than the material used to construct the cap 304. It will be appreciated that the tube 302 also can be constructed of a material having shape memory properties, so that when the tube 302 is temporarily deformed, for example to allow connection of the cap 304, the tube 302 can basically return to its original shape after the cap 304 has been connected or removed.

With further reference to the cap 304, in some embodiments an outer rim 314 extends beyond the outer diameter of the annular flange 310. Further, the cylindrical wall 326 has an edge surface 306 at the open end. As best shown in FIG. 14, the outer rim 314 has a surface that is engageable with the edge surface 306 to stop the cap 304 from fully entering the tube 302. In the embodiment shown, the surface of the outer rim 314 is perpendicular to the outer diameter of the annular flange 310, and the edge surface 306 of the cylindrical wall 326 is perpendicular to the inner diameter of the cylindrical wall 326. In such a configuration, the outer rim 314 and edge surface 306 are perpendicularly engageable to the inner diameter of the cylindrical wall 326 and the annular flange 310.

With further reference to the annular flange 310, the annular flange 310 in the embodiment shown also includes an inner diameter (see e.g. FIG. 14). A pocket 324 is formed by the end plate of the cap, and the inner diameter of the annular flange 310. The pocket 324 allows the cap to minimize the space or volume taken inside the tube 302 when the cap 304 is connected to the tube 302.

In some embodiments, the annular flange 310 can have a boost to help facilitate connection of the cap 304 to the tube 302. In the embodiment shown, the annular flange 310 has a leading end configured to enter the tube 302 first when the cap 304 is connected to the tube 302. In one embodiment, the leading end includes a ramp surface 312 extending away from the outer diameter. As shown, the ramp surface 312 extends annularly inward. Such a configuration can give the cap 304 a boost to help during connection of the cap 304 to the tube 302

Turning back to the closed end 318, the closed end 318 in the embodiment shown, is a plate structure at the end opposite the cap end. In some embodiments, the closed end 318 is of a material that is transparent 322 so as to allow one to see inside the tube 302 (see e.g. FIG. 12). The transparent quality of the closed end 318 can also allow for product promotion, labeling, and otherwise providing information about the kit and its contents. For instance, a sheet of promotional, labeling, or informational material (e.g. paper) could be bonded to the closed end 318 or loosely set adjacent the closed end 318 from the inside of the tube 302.

In some embodiments, the closed end 318 is a separate plate structure that is connected to the inner diameter of the cylindrical wall 326 at junction 320 (see e.g. FIG. 14). It will be appreciated that the closed end 318 can be integrally formed with the cylindrical wall 326. In many instances, the closed end 318, whether attached as a separate plate or integrally formed with the cylindrical wall 326, can be constructed of the same material as the cylindrical wall 326. It will be appreciated that the material of the closed end 318 can be different from the cylindrical wall 326 and, in some instances, could be a similar material as the cap 304. Turning back to the tube 302, it will be appreciated that the cylindrical wall 326 can be a material that is either opaque or transparent, but that it could be a material with a generic, or blank surface, that would allow support of unique product promotion, labeling, or placement of other information that may be related to the kit and its contents. For example, the cylindrical wall of the tube has an outer surface that is configured to supporting a product label. It will be further appreciated that the tube 302 is configured to allow the product label to be changed. For example, labeling could be a sheet of paper that can be placed around the outer surface of the cylindrical wall 326 of the tube 302, such as but not limited to being adhesively bonded to or tightly wrapped around the tube 302. The general structure of the cylindrical wall 326 allows the packaging 300 to accommodate various changes that may be needed for the labeling, for example different country requirements or regulations as to labeling and in various national languages. In some embodiments, the labeling can include a pink color. Likewise, the extra-labial voiding apparatus as described above can be a material of various colors. For example, the apparatus could be a pink color. Of course, it will be appreciated that other colors may be employed for both the labeling and the apparatus, which may or may not include the color pink. In some instances, the coloration (e.g. pink) could be more attractive to users and may suggest that the kit, its contents, as well as its packaging are more of an everyday consumer or cosmetic product and less of a prescribed medical device.

Various improvements upon existing female urine voiding devices have been described. Additionally, improvements to kits that include the urine voiding apparatuses described herein have been described, where such improvements include, but are not limited to, for example the overall packaging structure, user friendliness, and attractiveness of such kits.

With regard to the foregoing description, it is to be understood that changes may be made in detail, especially in matters of the construction materials employed and the shape, size, and arrangement of the parts. It is intended that the specification and depicted embodiments be considered exemplary only, with a true scope and spirit of the invention being indicated by the broad meaning of the following claims.

The invention claimed is:

1. An extra-labial urine voiding kit comprising:
   an extra-labia urine voiding apparatus;
   a piece of absorbent material;
   a bag configured for containing the extra-labial urine voiding apparatus and piece of absorbent material after usage; and
   a packaging structure comprising:
      a tube having a cylindrical wall, a closed end, and an open end, the cylindrical wall and closed end define a cavity configured to contain the extra-labial urine voiding apparatus, the absorbent material, and the bag before and after usage, the cylindrical wall has an inner surface defining an inner diameter; and
      a single cap connectable to and removable from the open end of the tube and adapted to respectively close and open the tube at the open end, the cap having an end plate with an annular flange extending therefrom, the annular flange has an outer surface defining an outer diameter, the annular flange being insertable into the cavity at the open end of the tube and within the inner diameter of the cylindrical wall,
      wherein the outer diameter of the flange being larger than the inner diameter of the cylindrical wall to a degree such that the outer diameter of the flange and the inner diameter of the cylindrical wall are engageable in a press-fit arrangement, when the cap is connected to the tube,
      the annular flange comprises an inner diameter, and the end plate and inner diameter of the annular flange form a pocket receivable of a portion of at least one of the extra-labia urine voiding apparatus, the piece of absorbent material, and the bag, and
      the closed end comprises a plate that is transparent to be adapted to see inside the tube.

2. The kit of claim 1, wherein the cavity of the tube is smaller in overall dimension than the extra-labial fluid voiding apparatus and the extra-labial fluid voiding apparatus is constructed of a shape memory material, such that the extra-labial urine voiding apparatus folds down to be contained in the tube.

3. The kit of claim 1, wherein the cylindrical wall is pliable and the annular flange is rigid.

4. The kit of claim 1, wherein the cap is an entirely rigid structure and the tube is less rigid than the cap.

5. The kit of claim 4, wherein the tube is constructed as a flexible material having shape memory.

6. The kit of claim 1, wherein the cap comprises an outer rim beyond the outer diameter of the annular flange, and the cylindrical wall comprises an edge surface at the open end, the outer rim having a surface that is engageable with the edge surface to stop the cap from fully entering the tube.

7. The kit of claim 6, wherein the surface of the outer rim is perpendicular to the outer diameter of the annular flange, and the edge surface of the cylindrical wall is perpendicular to the inner diameter of the cylindrical wall, such that the outer rim and edge surface are engageable perpendicularly to the inner diameter of the cylindrical wall and the annular flange.

8. The kit of claim 1, wherein the annular flange comprising a leading end configured to enter the tube first when the cap is connected to the tube, the leading end having a ramp surface extending annularly inward from the outer diameter.

9. The kit of claim 1, wherein the bag is constructed of a biodegradable material.

10. The kit of claim 1, wherein the bag comprises instructions for use disposed on an outer portion of the bag.

11. The kit of claim 1, wherein the tube having an outer surface configured for supporting a product label and configured such that the product label can be changed.

12. The kit of claim 11, wherein the labeling includes a pink color.

13. The kit of claim 1, wherein the apparatus is constructed of a pink color.

14. A packaging for an extra-labial fluid voiding apparatus comprising:

a tube having a cylindrical wall, a closed end, and an open end, the cylindrical wall and closed end define a cavity configured to contain the extra-labial urine voiding apparatus, an absorbent material, and a bag before and after usage, the cylindrical wall is pliable and has an inner surface defining an inner diameter; and a single cap connectable to and removable from open end of the tube and being adapted to respectively close and open the tube at the open end, the cap having an end plate with an annular flange extending therefrom, the annular flange is rigid and has an outer surface defining an outer diameter, the annular flange being insertable into the cavity at the open end of the tube and within the inner diameter of the cylindrical wall, wherein the outer diameter of the flange being larger than the inner diameter of the cylindrical wall to a degree such that the outer diameter of the flange and the inner diameter of the cylindrical wall are engageable in a press-fit arrangement, when the cap is connected to the tube, the annular flange comprises an inner diameter, and the end plate and inner diameter of the annular flange form a pocket receivable of a portion of at least one of the extra-labia urine voiding apparatus, the piece of absorbent material, and the bag, and the closed end comprises a plate that is transparent to be adapted to see inside the tube.

15. The packaging of claim 14, wherein the tube having an outer surface configured for supporting a product label and configured such that the product label can be changed.

16. The packaging of claim 15, wherein the labeling includes a pink color.

17. The kit of claim 1, wherein the closed end is integrally formed with the cylindrical wall.

18. The packaging of claim 14, wherein the closed end is integrally formed with the cylindrical wall.

* * * * *